United States Patent [19]

Schneider

[11] Patent Number: 5,905,074

[45] Date of Patent: May 18, 1999

[54] VITAMIN D DERIVATIVE

[75] Inventor: Fernand Schneider, Basle, Switzerland

[73] Assignee: Hoffmann-La Roche Inc., Nutley, N.J.

[21] Appl. No.: 08/993,851

[22] Filed: Dec. 18, 1997

Related U.S. Application Data

[63] Continuation of application No. 08/731,039, Oct. 8, 1996, abandoned.

[30] Foreign Application Priority Data

Oct. 30, 1995 [EP] European Pat. Off. .............. 95117037

[51] Int. Cl.$^6$ ........................... A61K 31/59; C07C 401/00
[52] U.S. Cl. ........................ 514/167; 514/715; 514/729; 552/653; 568/665; 568/819; 556/9; 556/12
[58] Field of Search ..................... 514/167, 715, 514/729; 552/653; 568/665, 819; 556/9.12

[56] References Cited

U.S. PATENT DOCUMENTS

| | | | |
|---|---|---|---|
| 3,697,559 | 10/1972 | DeLuca et al. | 552/653 |
| 4,410,515 | 10/1983 | Holick et al. | 428/180 |
| 4,521,410 | 6/1985 | Holick et al. | 514/26 |
| 4,595,776 | 6/1986 | Baggiolini et al. | 556/436 |
| 5,422,365 | 6/1995 | Billington et al. | 514/468 |
| 5,525,745 | 6/1996 | DeLuca et al. | 552/653 |

FOREIGN PATENT DOCUMENTS

95/01960 1/1995 WIPO .

OTHER PUBLICATIONS

Chen et al. Synthesis of New Vitamin $D_3$ Analogs with a decalin–type CD ring. Chem. Abstr. No. 126: 104299 (1966).

*Primary Examiner*—Deborah C. Lambkin
*Attorney, Agent, or Firm*—George W. Johnson; Patricia S. Rocha-Tramaloni; Robert A. Silverman

[57] ABSTRACT

A compound of the formula

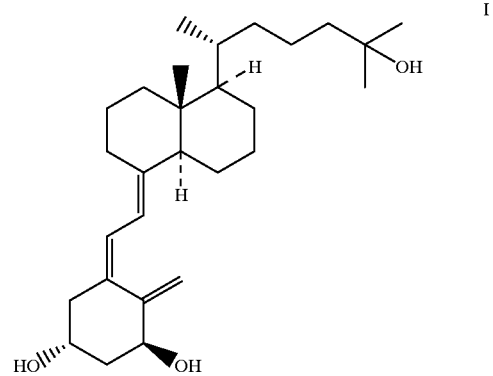

useful for treating vitamin D dependent disorders.

7 Claims, No Drawings

VITAMIN D DERIVATIVE

This application is a continuation of Ser. No. 08/731,039 Oct. 8, 1996, abandoned.

BRIEF SUMMARY OF THE INVENTION

The present invention relates to a novel vitamin D derivative. More particularly, the invention relates to 1α,26-dihydroxy-D-homo-vitamin $D_3$ of the formula I

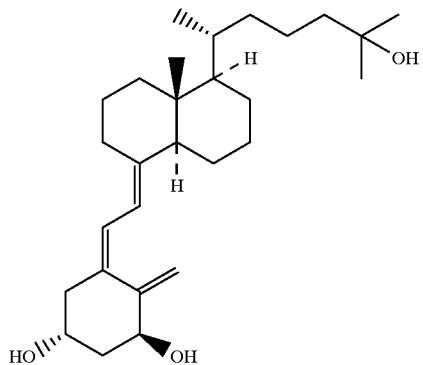

The systematic nomenclature of the compound of formula I is (1R,3S)-5-[(Z)-2-[(E)-(4aR,5R,8aR)-5-[(R)-5-Hydroxy-1,5-dimethyl-hexyl]-4a-methyl-octahydro-naphtalen-1-ylidene]-ethylidene]-4-methylene-cyclohexane-1,3-diol.

The present invention furthermore relates to a process for the preparation of the compound of formula I, pharmaceutical compositions containing the compound of formula I, and the use of the compound of formula I for the treatment of vitamin D dependent disorders and for the manufacture of pharmaceutical compositions for the treatment of vitamin D dependent disorders.

DETAILED DESCRIPTION OF THE INVENTION

The invention relates to 1α,26-dihydroxy-D-homo-vitamin $D_3$ of the formula I

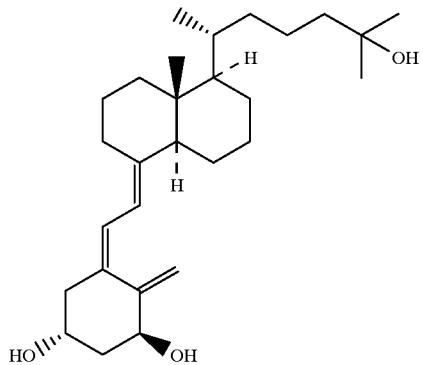

The systematic nomenclature of the compound of formula I is (1R,3S)-5-[(Z)-2-[(E)-(4aR,5R,8aR)-5-[(R)-5-Hydroxy-1,5-dimethyl-hexyl]-4a-methyl-octahydro-naphtalen-1-ylidene]-ethylidene]-4-methylenecyclohexane-1,3-diol.

The present invention furthermore relates to a process for the preparation of the compound of formula I, pharmaceutical compositions containing the compound of formula I, and the use of the compound of formula I for the treatment of vitamin D dependent disorders and for the manufacture of pharmaceutical compositions for the treatment of vitamin D dependent disorders.

The term "vitamin D dependent disorders" refers to disorders which can be treated or prevented by the administration of compounds having vitamin D activity, such as vitamin $D_3$ or derivatives, in particular hydroxylated derivatives thereof, for example, calcitriol or calcipotriol. Examples of such disorders are hyperproliferative skin diseases such as psoriasis; neoplastic diseases such as leukemia; disorders of the sebaceous glands such as acne and seborrhoic dermatitis; osteoporosis; and hyperparathyroidism accompanying renal failure.

The compound of formula I can be prepared as set forth in formula schemes 1 and 2 below:

According to Scheme 1, compound (1) [Synthesis 957 (1993)] is reduced to yield the equatorial alcohol (2), which is transformed to (4) via the thiocarbamate (3). Compound (4) can be hydroborated to yield (5). Oxidation of the alcohol, for example, with pyridiniumchlorochromate and equilibration with potassium-tertio-butoxide yields (6), which can be reduced to give compound (7). Acetylation of (7) and cleavage of the tert.-butyl ether function yields (8) which is oxidized and deacylated to yield ketoalcohol (9). For build-up of the vitamin $D_3$ side chain the alcohol group of (9) is suitably protected, for example, by a silyl ether protecting group Z, to obtain (10).

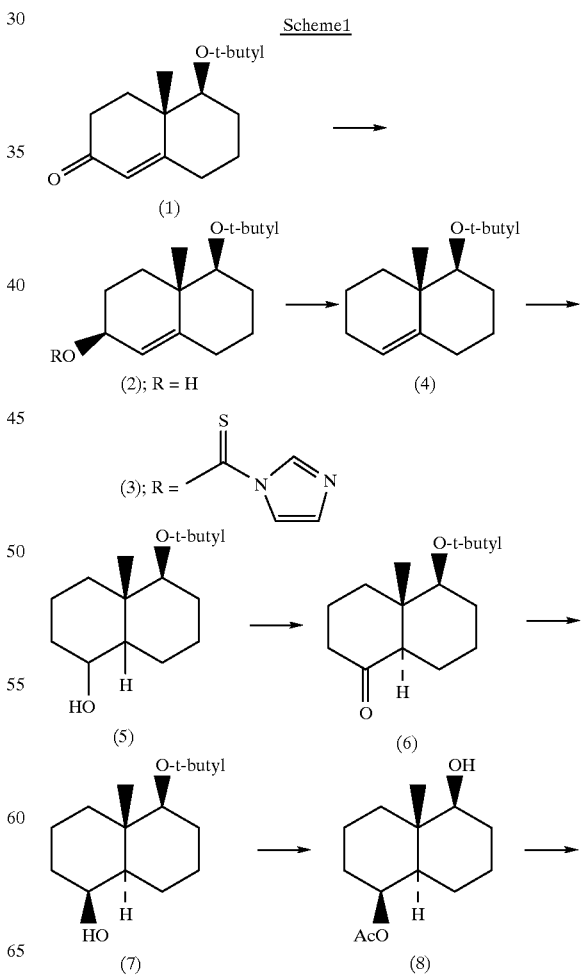

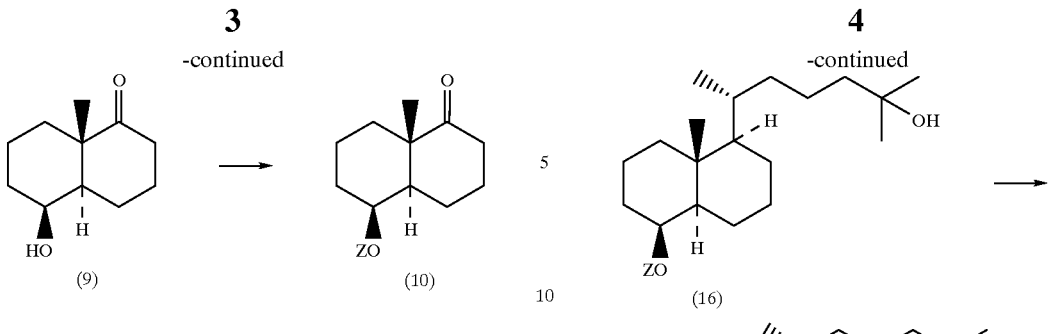

According to Scheme 2, ketone (10) is converted by a Wittig reaction into compound (11) from which (12) is obtained by an ene reaction with paraformaldehyde and dimethylaluminium chloride. Catalytic hydrogenation of (12) gives (13), from which (15) is obtained via the iodide (14) by chain extension with ethyl acrylate. From (15) tert. alcohol (16) can be obtained by a Grignard reaction. Cleavage of the protecting group Z finally yields (17).

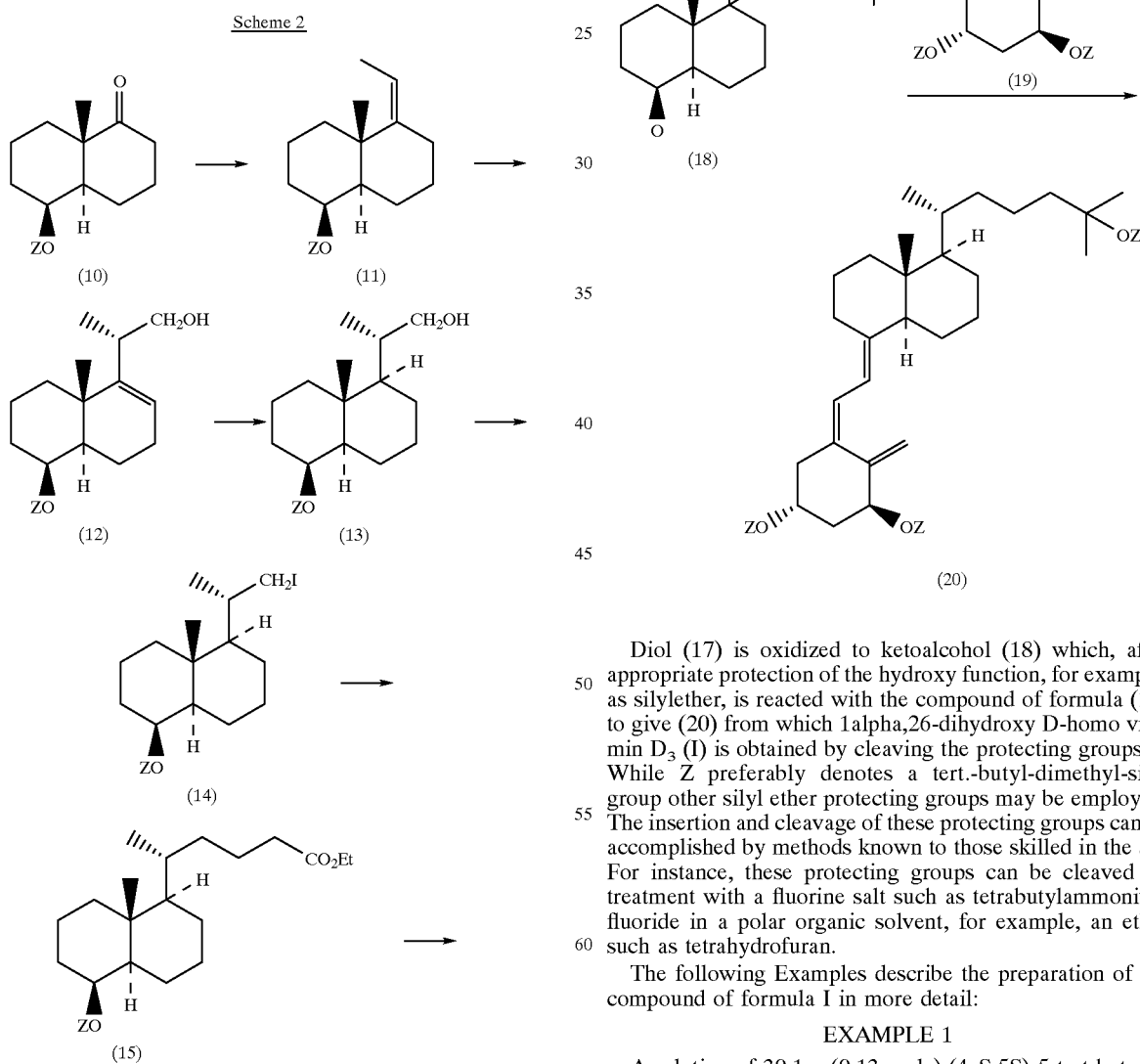

Diol (17) is oxidized to ketoalcohol (18) which, after appropriate protection of the hydroxy function, for example, as silylether, is reacted with the compound of formula (19) to give (20) from which 1alpha,26-dihydroxy D-homo vitamin $D_3$ (I) is obtained by cleaving the protecting groups Z. While Z preferably denotes a tert.-butyl-dimethyl-silyl group other silyl ether protecting groups may be employed. The insertion and cleavage of these protecting groups can be accomplished by methods known to those skilled in the art. For instance, these protecting groups can be cleaved by treatment with a fluorine salt such as tetrabutylammonium fluoride in a polar organic solvent, for example, an ether such as tetrahydrofuran.

The following Examples describe the preparation of the compound of formula I in more detail:

EXAMPLE 1

A solution of 30.1 g (0.13 mole) (4aS,5S)-5-tert-butoxy-4a-methyl-4,4a,5,6,7,8-hexahydro-2(3H)-naphtalenone in 600 ml tetrahydrofuran was cooled under stirring and Argon atmosphere to −78° C. After dropwise addition of 140 ml (0.14 mole) of L-selectride.(1 molar in tetrahydrofuran), the reaction mixture was kept at −78° C. for an additional hour, then warmed to room temperature and kept at this temperature for 4.5 hours. After cooling to −15° C., 12 ml of $H_2O$, 90 ml of 4N NaOH and 100 ml of $H_2O_2$ (30%) were added sequentially and dropwise by keeping the temperature between −10° C. to −15° C. After the addition is complete, the reaction mixture was warmed to room temperature, poured onto water and extracted three times with ethylacetate. The combined organic layers were dried with sodium sulfate and evaporated after filtration to yield 30 g of crude (2S,4aS,5S)-5-tert-Butoxy-4a-methyl-2,3,4,4a,5,6,7,8-octahydrohydro-naphatalen-2-ol as an amorphous product shown by thin layer chromatography and NMR to be sufficiently pure for further transformations.

EXAMPLE 2

To a solution of 13 g (54.54 mMol) (2S,4aS,5S)-5-tert-Butoxy-4a-methyl-4,4a,5,6,7,8-octahydro-naphtalen-2-ol in 150 ml tetrahydrofuran were added 20 g (112 mMol) of 1,1'-thiocarbonyldiimidazole. The reaction mixture was refluxed for two hours, cooled to room temperature and evaporated in vacuo. The residue was chromatographed over silica gel with hexane/ethylacetate 4/1 and gave 14.8 g of imidazole-1-carbothioic acid(2S, 4aS, 5S)-O-(5-tert-butoxy-4a-methyl-2,3,4,4a,5,6,7,8-octahydro-naphtalen-2-yl)ester as an amorphous material.

EXAMPLE 3

To a stirred solution of 9.95 g (28.5 mMol) imidazole-1-carbothioic acid(2S, 4aS, 5S)-O-(5-tert-butoxy-4a-methyl-2,3,4,4a,5,6,7,8-octahydro-naphtalen -2-yl)ester in 285 ml toluene kept under argon atmosphere were added 75.7 ml (285 mMol) of tributyltinhydride and 75.7 ml of a one molar solution of triethylborane in tetrahydrofuran. The reaction mixture was heated to 120° C. for 4 hours and additional 20 ml of tributyltinhydride as well as 20 ml of triethylborane solution (one molar in tetrahydrofuran) were added. The reaction mixture was kept at 120° C. for 3 days, cooled to room temperature and evaporated in vacuo. The residue was chromatographed twice over 900 g silica gel with toluene/hexane 1/1 to yield 4.3 g of pure (4S,4aS)-4-tert-Butoxy-4a-methyl-1,2,3,4,4a,5,6,7-octahydro-naphtalene (liquid).

EXAMPLE 4

A solution of 6.15 g (27.6 mMol) of (4aS, 4aS)-5-tert-Butoxy-4a-methyl-1,2,3,4,4a,5,6,7-octahydro-naphtalene in 180 ml tetrahydrofuran was cooled under argon atmosphere and stirring to 0° C. 55.3 ml (55.3 mMol) of a one molar solution of borane in tetrahydrofuran was added, the reaction mixture kept for an additional hour at 0° C., warmed to room temperature and kept stirring overnight. After cooling to 0° C., 421 ml of water were added dropwise, followed by addition of 25.3 g $NaBO_3.4H_2O$. The suspension was stirred at room temperature for 4 hours, then the reaction mixture was extracted three times with diethylether. The combined organic phases were washed once with brine, dried over sodium sulfate and evaporated in vacuo to yield 12.07 g of crude product, which was chromatographed over 500 g silica gel with hexane/ethylacetate 4/1 to give 3.4 g of a 2:1 Mixture of (1S,4aS,5S,8aS)-and (1R,4aS,5S,8aR)-5-tert-butoxy-4a-methyl-decahydro-naphtalen-1-ol as an oily material.

EXAMPLE 5

To a solution of 3.4 g (14.1 mMol) of (1RS,4aS,5S,8aRS)-5-tert-Butoxy-4a-methyl-decahydro-naphtalen-1-ol in 34 ml methylenechloride was added under stirring 3.66 g (17.0 mMol) of pyridiniumchlorochromate and the reaction mixture was kept under stirring overnight. Then the reaction was diluted with 33 ml diethylether, kept stirring for 15 minutes and filtered over florisil®. The filtrate was evaporated to dryness in vacuo and the residue dissolved in 33 ml of tetrahydrofuran. Under stirring and argon atmosphere, 1.65 ml of a one molar solution of potassium-tertio-butoxide in tetrahydrofuran was added and the reaction was kept overnight. This equilibration is monitored by TLC ( silica gel, hexane/ethylacetate 4/1), which shows the almost complete disappearance of one of the two epimers. The reaction mixture is evaporated in vacuo to dryness, the residue is taken up in water and extracted three times with diethylether. The combined organic phase is washed with water and brine, dried over sodium sulfate and evaporated in vacuo. The residue is chromatographed over 120 g of silica gel with hexane/ethylacetate 9/1 to yield 2.39 g (71%) of pure (4aS,5S,8aR)-5-tert-Butoxy-4a-methyl-octahydro-naphtalen-1-one. An analytical sample was obtained by crystallization from hexane with a m.p. of 78–79° C.

EXAMPLE 6

A solution of 2.12 g (8.9 mMol) of (4aS,5S,8aR)-5-tert-Butoxy4a-methyl-octahydro-naphtalen-1-one in 44.5 ml tetrahydrofuran was cooled to −78° C. and 9.8 ml (9.8 mMol) of a one molar solution of L-selectride in tetrahydrofuran was added dropwise under stirring and argon atmosphere. The reaction mixture was kept at this temperature for an additional hour, warmed to room temperature and kept overnight. The temperature was then lowered to −15° C. and 0.17 ml of $H_2O$ were added dropwise. This was followed by dropwise addition of 7.60 ml 3N NaOH and 6.36 ml of $H_2O_2$. The reaction temperature is kept between −10 to −15° C. The reaction mixture is then poured into water and extracted three times with ethylacetate. The combined organic extracts are washed with brine and evaporated in vacuo to dryness. The residue is chromatographed over 120 g of silicagel with hexane/ethylacetate 4/1 to yield 1.03 g (48%) of pure (1S,4aS,5S,8aR)-5-tert-Butoxy-4a-methyl-decahydronaphtalen-1-ol as an amorphous product.

EXAMPLE 7

A solution of 4.11 g (17.1 mMol) of (1S,4aS,5S,8aR)-5-tert-Butoxy-4a-methyl-decahydro-naphtalen-1-ol and 313.6 mg (2.6 mMol) of 4-dimethylaminopyridine in 26 ml of pyridine is treated with 13 ml of acetic anhydride under stirring and argon atmosphere for two hours. The reaction mixture is poured on ice-water and extracted three times with diethylether. The combined organic layer is washed twice with water, dried over sodium sulfate and evaporated in vacuo to yield 1.26 g of crude product which is chromatographed over 60 g of silicagel with hexane/ethylacetate 9/1 to give 4.64 g (91%) of Acetic acid (1S,4aS,5S,8aR)-5-tert-butoxy-4a-methyl-decahydronaphtalen -1-yl ester as an amorphous pure product.

EXAMPLE 8

A solution of 4.08 g (14.45 mMol) of acetic acid (1S, 4aS,5S,8aR)-5-tert-Butoxy-4a-methyl-decahydronaphtalen-1-yl ester in 7.25 ml of carbon tetrachloride is treated dropwise under stirring and argon atmosphere with 2.56 ml (18.8 mMol) of trimethylsilyliodide by keeping room temperature. After the addition is complete, the reaction mixture is stirred for another 30 minutes, then 1.79 ml of methanol are added and the reaction kept for 15 minutes. The reaction mixture is evaporated in vacuo to dryness to yield 5.52 g. The residue is chromatographed over 500 g of silica gel with hexane/ethylacetate 4/1 to give 2.88 g (88%) of pure acetic acid (1S,4aS,5S,8aR)-5-hydroxy-4a-methyl-decahydronaphtalen-1-yl ester.

EXAMPLE 9

3.73 g (17.3 mMol) of pyridinium chlorochromate is added under stirring to a solution of 3.25 g (14.35 mMol) of acetic acid (1S,4aS,5S,8aR)-5-Hydroxy-4a-methyl-decahydro-naphtalen-1-yl ester in 32.5 ml of dichloromethane. The reaction mixture is stirred overnight, diluted with 70 ml of diethylether, stirred for 15 minutes and filtered over florisil using diethylether for thorough elution. Evaporation in vacuo yields 3.34 g of a residue, which is chromatographed over 200 g of silica gel with hexane/ethylacetate 4/1 to give 3.02 g (94%) of pure acetic acid (1S,4aS,8aR)-4a-methyl-5-oxo-decahydronaphtalen-1-yl ester as an oil.

EXAMPLE 10

A solution of 2.99 g (13.3 mMol) of acetic acid (1S,4aS,8aR)-4a-methyl-5-oxo-decahydro-naphtalen-1-yl ester in 13.3 ml of ethanol is treated under stirring and argon atmosphere with sodium ethylate prepared from 0.67 g (29.4 g/atom) of sodium and 29.4 ml of ethanol and the reaction mixture is kept overnight. The solvent is evaporated in vacuo to dryness, the residue is taken up in water and after cooling to 0° C., the pH is adjusted to 3–4 with 1N HCl. After extracting three times with diethylether, the combined organic extract is washed with brine, dried with sodium sulfate and the solvent is evaporated in vacuo. The residue is triturated with hexane, the crystals are filtered off and dried: 1.07 g (95%) of pure (4aR,5S,8aS)-5-Hydroxy-8a-methyl-octahydro-naphtalen-1-one m.p.:109.5–111° C.

EXAMPLE 11

To a solution of 2.3 g (12.6 mMol) of (4aR,5S,8aS)-5-Hydroxy-8a-methyl-octahydro-naphtalen-1-one in 63 ml of dimethylformamide are added under stirring and argon atmosphere 3.74 g (24.8 mMol) of tertio-butyl-dimethyl-silychloride and 1.94 g (28.5 mMol) of imidazole. The reaction mixture is heated to 100° C. for 4 hours, then additional 3.74 g of tert-butyl-dimethyl-silylchloride and 1.94 g of imidazole are added and the reaction mixture is kept overnight at 100° C. The reaction mixture is poured onto ice-water and extracted three times with diethylether. The combined organic extract is washed once with water and brine, dried over sodium sulfate and evaporated in vacuo. The residue is chromatographed over 250 g of silica gel with hexane/ethylacetate 9/1 to yield 3.17 g (85%) of low melting crystalline (4aR,5S,8aS)-5-(tert-Butyl-dimethyl-silanyloxy)-8a-methyl-octahydro-naphtalen-1-one.

EXAMPLE 12

A suspension of 11.8 g (31.7 mMol) of ethyltriphenylphosphoniumbromide in 64 ml of tetrahydrofuran is treated under stirring and argon atmosphere with 31.9 ml of a one molar solution of potassiumtertiobutylate and the resulting orange suspension treated with a solution of 3.17 g (10.7 mMol) of (4aR,5S,8aS)-5-(tert-Butyl-dimethyl-silanyloxy)-8a-methyl-octahydro-naphtalen-1-one in 64 ml of tetrahydrofuran and kept at room temperature for 3 hours. An additional 11.8 g (31.7 mMol) of ethyltriphenylphosphoniumbromid and 31.9 ml of a one molar solution of potassiumtertiobutylate in tetrahydrofurane are added and the reaction mixture kept overnight. Isobutyraldehyde (5.4 ml) is added, the reaction is stirred for 10 minutes, diluted with diethylether and filtered over Florisil using diethylether as eluent. After evaporation in vacuo, the residue (4.79 g) is chromatographed over 120 g of silica gel with hexane to yield 3.15 g (95%) of pure (1S,4aS,8aR)-tert-Butyl-(5-ethylidene-4a-methyl-decahydro-naphtalen-1-yloxy)-dimethyl-silane (E/Z 4/1) as an oil.

EXAMPLE 13

To a stirred solution of 3.11 g (10.1 mMol) of (1S,4aS,8aR)-tert-Butyl-(5-ethylidene-4a-methyl-decahydro-naphtalen-1-yloxy)-dimethylsilane in 125 ml of toluene are added 0.33 g (11.1 mMol) of finely powdered paraformaldehyde. The reaction mixture is cooled to 0° C. and 12.56 ml of a one molar solution of dimethylaluminumchloride in hexane are added and kept for one hour at this temperature. The reaction mixture is stirred at room temperature overnight, diluted with diethylether, washed with 1N HCl and with water, then dried over sodium sulfate and evaporated in vacuo. The residue is chromatographed over a medium pressure 250 g silica gel column with hexane/ethylacetate 9/1 to yield 2.31 g (67.5%) of pure (S)-2-[(4aR,5S,8aS)-5-(tert-Butyl-dimethyl-silanyloxy)-8a-methyl-3,4,4a,5,6,7,8,8a-octahydro-naphtalen-1-yl]-propan-1-ol as an oil.

EXAMPLE 14

To a solution of 2.27 g (6.7mMol) of (S)-2-[(4aR,5S,8aS)-5-(tert-butyl-dimethyl-silanyloxy)-8a-methyl-3,4,4a,5,6,7,8,8a-octahydro-naphtalen-1-yl]-propan-1-ol in 22.7 ml of ethylacetate were added 227 mg of Pd/C 10% and 227 mg of sodium bicarbonate. The reaction mixture was stirred under hydrogen atmosphere overnight, filtered over Speedex using ethylacetate for washing thoroughly and the solvent evaporated in vacuo. The residue was chromatographed over a 250 g Lobar column with hexane/ethylacetate 9/1 to yield 2.18 g (95.5%) of (S)-2-[(1R,4aR,5S,8aR)-5-(tert-Butyl-dimethyl-silanyloxy)-8a-methyl-decahydro-naphtalen-1-yl]-propan-1-ol as an oily product.

EXAMPLE 15

To a solution of 485 mg (1.35 mMol) of (S)-2-[(1R,4aR,5S,8aR)-5-(tert-Butyl-dimethyl-silanyloxy)-8a-methyl-decahydro-naphtalen-1-yl]-propan-1-ol in 10 ml of $CH_2Cl_2$ are added under stirring 216.3 mg (3.17 mMol) of imidazole and 704.4 mg (2.68 mMol) of triphenylphosphin. The reaction mixture is cooled to −10° and 681.6 mg (2.68 mMol) of iodine are added portionwise. The reaction mixture is kept at −10° for ½ hour, then warmed to room temperature and stirred overnight. The reaction is quenched with 0.3 ml of ethanol, stirred for ½ hour and treated with a solution of 300 mg of Na thiosulfate in 0.3 ml of water. The slurry obtained after evaporation in vacuo is extracted three times with diethylether. The combined extracts are washed with water, dried over $Na_2SO_4$, filtered and evaporated. The residue is chromatographed over silicagel (25 g) with hexane/ethylacetate 9/1 to yield. 563 mg (93%) of (1S,4aR,5R,8aR)-tert-Butyl-[5-[(S)-2-iodo-1-methyl-ethyl]-4a-methyl-decahydronaphtalen-1-yloxy]-dimethyl-silane as an amorphous product.

EXAMPLE 16

To 342.5 mg (5.24 mMol) of Zn powder are added 1.57 ml of tetrahydrofuran/pyridine 2/1. The reaction mixture is stirred under Argon, 247.2 mg (1.04 mMol) of $NiCl_2.6H_2O$ and then 472.2 mg (4.72 mMol) of ethylacrylate are added. The reaction mixture is heated at 65° for 30 minutes, cooled to room temperature and 947 mg (2.10 mMol) of (1S,4aR,5R,8aR)-tert-Butyl[5-[(S)-2-iodo-1-methyl-ethyl]-4a- methyl-decahydronaphtalen-1-yloxy]-dimethylsilane dissolved in 1.57 ml of tetrahydrofuran pyridine ½ are added and the reaction mixture kept overnight at room temperature. Filtration through Speedex and washing of the filter cake with ethylacetate is followed by evaporation in vacuo to ⅓ of the volume. The solution is diluted with ethylacetate and the organic phase is washed 4 times with a disodium ethylene diamine tetraacetate dihydrate (EDTA) solution (8 g of EDTA and 8 g of NaHCO$_3$ in 100 ml water) and twice with brine. The organic phase is dried over Na$_2$SO$_4$, filtered and evaporated in vacuo. The residue is chromatographed over 100 g of silicagel with hexane/ethylacetate 98/2 to yield 269 mg of starting material and 390 mg (44%) of (R)-5-[(1R,4aR,5S,8aR)-5-(tert-Butyl-dimethyl-silanyloxy)-8a-methyl-decahydro-naphtalen-1-yl)-hexanoic acid ethyl ester as an amorphous product.

EXAMPLE 17

A solution of 360 mg (0.85 mMol) of (R)-5-[(1R,4aR,5S,8aR)-5-[5-(tert-Butyl-dimethyl-silanyloxy)-8a-methyl-decahydro-naphtalen-1-yl)-hexanoic acid ethyl ester in 5 ml of absolute tetrahydrofuran is cooled to 0° under stirring and Argon atmosphere. After addition of 1.6 ml (4.54 mMol) of a solution of CH$_3$ MgCl in tetrahydrofuran (22%), the reaction mixture is warmed to room temperature and kept for 3 hours. The cooled reaction mixture (ice bath) is quenched with saturated aqueous NH$_4$Cl solution, diluted with ethylacetate and the separated organic phase is washed with brine, water, dried over Na$_2$SO$_4$, filtered and evaporated in vacuo. The crude product is chromatographed over silicagel (80 g) with hexane/ethylacetate 9/1 to give 202 mg (58%) of (R)-6-[(1R,4aR,5S,8aR)-5-(tert-Butyl-dimethyl-silanyloxy)-8a-methyl-decahydronaphtalen-1-yl]-2-methyl-heptan-2-ol as an amorphous product.

EXAMPLE 18

To a stirred solution of 267 mg (0.65 mMol) of (R)-6-[(1R,4aR,5S,8aR)-5-(tert-butyl-dimethyl-silanyloxy)-8a-methyl-decahydronaphtalen-1-yl]-2-methyl-heptan-2-ol in 2.5 ml of tetrahydrofuran are added 7.5 ml of acetonitrile and 2.5 ml of an aqueous HF solution (40%). The reaction mixture is kept for 72 hours, poured unto water and extracted three times with diethylether, the combined organic extracts are washed with a saturated aqueous NaHCO$_3$ solution, with water, dried over Na$_2$SO$_4$, filtered and evaporated in vacuo. The residue is chromatographed over 40 g of silicagel with toluene/diethylether 4/1 to yield 107 mg (56%) of crystalline pure (1S,4aR,5R,8aR)-5-[(R)-5-Hydroxy-1,5-dimethyl-hexyl]-4a-methyl -decahydro-naphtalen-1-ol. The material crystallized with diisopropylether has m.p.: 85.1–86.9°.

EXAMPLE 19

To a solution of 104 mg (0.35 mMol) of (1S,4aR,5R,8aR)-5-[(R)-5-Hydroxy-1,5-dimethyl-hexyl]-4a-methyl-decahydro-naphtalen-1-ol in 2 ml of CH$_2$Cl$_2$ are added under stirring 91.5 mg (0.42 mMol) of pyridiniumchlorochromate. The reaction mixture is kept stirring for 4 hours, diethylether is added and the slurry is filtered through Florisil using diethylether as eluant. The residue obtained after evaporation in vacuo is chromatographed over 5 g of silicagel with CH$_2$Cl$_2$/ethylacetate 9/1 to yield 88 mg (85.5%) of oily pure (4aR,5R,8aR)-5-[(R)-5-Hydroxy-1,5-dimethyl-hexyl]-4a-methyl-octahydro-naphtalen-1-one.

EXAMPLE 20

A solution of 24 mg (0.08 mMol) of (4aR,5R,8aR)-5-[(R)-5-Hydroxy-1,5-dimethyl-hexyl]-4a-methyl-octahydro-naphtalen-1-one in 0.5 ml of tetrahydrofuran is cooled under stirring and Argon atmosphere to 0°. The reaction mixture is stirred for an additional hour after addition of 12 μl (0.08 mMol) of trimethylsilylimidazole, of 5.1 μl (0.04 mMol) of trimethylsilylchloride and of 2.8 mg (0.04 mMol) of imidazole. The reaction mixture is poured into ice water, extracted three times with diethylether, the combined organic extracts are washed twice with brine and dried over Na$_2$SO$_4$. The organic solvent is evaporated in vacuo and the residue is chromatographed over 5 g of silicagel with hexane/diethylether 9/1 to yield 25 mg of pure, oily (4aR,5R,8aR)-5-[(R)-1,5-Dimethyl-5-trimethylsilanyloxy-hexyl]-4a-methyl -octahydro-naphtalen-1-one

EXAMPLE 21

To a solution stirred under Argon of 134 mg (0.23 mMol) of [3S-(3 alpha, 5 beta, Z)]-2-(2-[2-methylene-3,5-bis[[(1,1-dimethylethyl)dimethylsilyl]oxy]cyclohexylidene]ethyl] diphenylphosphine oxide in 0.9 ml of tetrahydrofuran, cooled to −78° are added slowly 143 μl (0.23 mMol) of BuLi solution in hexane (1.6M). The reaction mixture is kept at this temperature for 30 minutes, then a solution of 40.2 mg (0.11 mMol) of (4aR,5R,8aR)-5-[(R)-1,5-Dimethyl-5-trimethylsilanyloxy-hexyl)-4a-methyl-octahydro-naphtalen-1-one in 0.9 ml of tetrahydrofuran is added with a syringe. After additional 30 minutes at −78°, the reaction mixture is heated to room temperature within 2 hours. The reaction is quenched at 0° with 2 ml of an aqueous NaHCO$_3$ solution (5%), poured into brine and extracted three times with diethylether. The combined organic extracts are washed twice with brine, dried over Na$_2$SO$_4$, filtered and evaporated in vacuo. The residue is chromatographed over 20 g of silicagel with hexane/diisopropylether 19.5/0.5 to yield 21 mg of impure silylated product (TLC silicagel, CH$_2$Cl$_2$/ethylacetate 9/1, Rf=0.74). This material is dissolved in 0.2 ml of tetrahydrofuran under Argon and 0.1 ml of tetrabutylammoniumfluoride solution in tetrahydrofuran (1M) is added. The reaction is kept at room temperature overnight, evaporated in vacuo and the residue is chromatographed over 5 g of silicagel with ethylacetate/hexane 4/1 to yield 11.5 mg of crystalline material, which is recrystallized from ethylacetate/hexane to give 5 mg of pure, crystalline (1R, 3S)-5-[(Z)-2-[(E)-(4aR,5R,8aR)-5-[(R)-5-Hydroxy-1,5-dimethyl-hexyl]-4a-methyl-octahydro-naphtalen-1-ylidene]-ethylidene]-4-methylenecyclohexane -1,3-diol (1α,26-dihydroxy-D-homo-vitamin D$_3$,I), m.p.: 124–127°.

The pharmacological properties of the compounds of the formula I can be determined by the following test procedures:

1. VDR activation

In order to measure the activation of the vitamin D receptor (VDR) by vitamin D analogs in cells a transcription activation assay was used. COS cells or CV-1 cells were cotransfected with the human VDR (expressed in pSG5) and a reporter gene containing three response elements (VDRE3) from the rat osteocalcine gene, the thymidine kinase basal promoter, and the luciferase reporter gene.

In this system, the activity of the test compound is expressed as the concentration which leads to half-maximal induction (EC$_{50}$) of the luciferase activity (maximal induction is 8–10 fold).

2. HL-60 differentiation

The induction of differentiation of HL-60 cells was assayed by measuring their oxidative burst potential via the reduction of NBT (Nitro-bluetetraolium) according to a modified procedure of E. Pick et al. in J. Reticul. Soc. 30, 581 (1981).

HL-60 cells were maintained in RPMI 1640 medium supplemented with 10% FCS, 2 mM L-glutamine, 1 mM sodium pyruvate, 1% nonessential amino acids, 50 U/ml penicillin and 50 μg/ml streptomycin (=RPMI/FCS). 30,000 cells/90 μl of RPMI/FCS were seeded into flat-bottomed microtiter wells. Immediately after seeding, 10 μl of vitamin D derivatives diluted in complete medium (RPMI/FCS) were added to yield final concentrations between $10^{-11}$ and $10^{-6}$M (starting from 1 mM stock solutions in ethanol which were stored at −20° and protected from light). After 3 days, the medium was removed with a multichannel pipette and replaced with 100 μl of NBT solution (1 mg/ml in Dulbecco's PBS with 200 nM phorbol myristate acetate (PMA)). Following an incubation of 1 hour at 37° C. the NBT solution was removed and 100 μl of 10% SDS in 0.01N HCl was added. After further incubation at 37° C. for 6 hours (or more), the amount of the reduced NBT was quantified photometrically at 540 nm using an automated plate reader. The mean of 3 wells was calculated.

Values were expressed as percent of maximal differentiation achieved with 100–1000 nM calcitriol in the same experiment. The concentration (nM) leading to 50% of this maximal value is determined graphically and given as $EC_{50}$.

3. Calcium liability (tolerance test in mice)

This routine test gives a global picture of calcemic liability. Profound changes in calcium homeostasis strongly affect the weight development of the animals. This parameter was used as a primary test for tolerance.

Mice (25–30 g body weight) received daily subcutaneous administrations of the vitamin D derivative for 4 consecutive days. Body weight was registered just before and at the end of a 5 day treatment period. The "highest tolerated dose" (HTD) in mice is the dose which results in zero weight gain during this treatment period.

The results obtained with the compound of formula I and with calcitriol in these tests procedures are shown below:

| Compound | VDR activation $EC_{50}$ [nM] COS cells/CV-1 cells | HL-60 differentiation $EC_{50}$ [nM] | highest tolerated dose (mice) [μg/kg] |
|---|---|---|---|
| Calcitriol | 2.8/0.14 | 5 | 0.5 |
| Compound of formula I | 1.2/0.04 | 0.37 | 0.6 |

The compound of formula I can be administered orally, for the treatment of neoplastic diseases such as leukemia and for the treatment of osteoporosis and hyperparathyroidism, to warmblooded animals which need such treatment, for example, to an adult human in dosages that are in the range of about 0.1 to 10 μg per day. The compound of formula I can also be administered topically or orally for the treatment of hyperproliferative skin diseases such as psoriasis, basal cell carcinomas, disorders of keratinization, and keratosis, to warmblooded animals which need such treatment, for example, to an adult human in dosages that are in the range of about 5–50 μg per gram of topical formulation per day.

The following pharmaceutical compositions can be prepared in a known manner:

EXAMPLE A

| Oral Dosage Form Soft Gelatin Capsule | mg/Capsule |
|---|---|
| Compound I | 0.0001–0.010 |
| Butylated Hydroxytoluene (BHT) | 0.016 |
| Butylated Hydroxyanisole (BHA) | 0.016 |
| Fractionated Coconut Oil (Neobee M-5) | 160.0 |

EXAMPLE B

| Topical Cream | mg/g |
|---|---|
| Compound I | 0.005–0.050 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. |

EXAMPLE C

| Topical ointment | mg/g |
|---|---|
| Compound I | 0.005–0.050 |
| Propylenglycol | exc. ad ung. pro 1 g |

I claim:

1. The compound of formula I

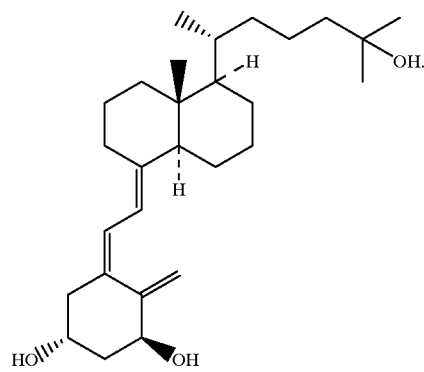

2. A compound of the formula

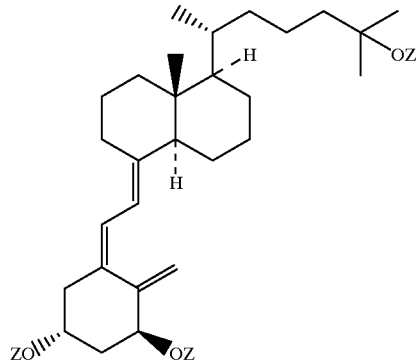

wherein Z is a protecting group.

3. The compound of claim 2 wherein the protecting group is a silyl ether protecting group.

4. A pharmaceutical composition, comprising an effective amount of the compound of formula I

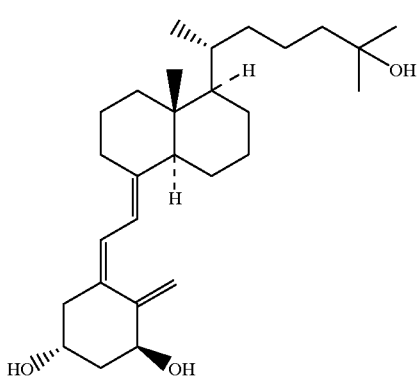

and a pharmaceutically acceptable carrier.

5. A process for the manufacture of the compound of formula

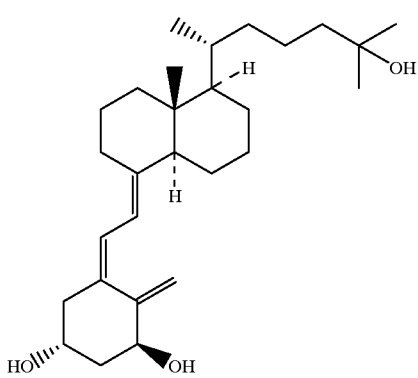

which process comprises cleaving the protecting group Z in a compound of formula

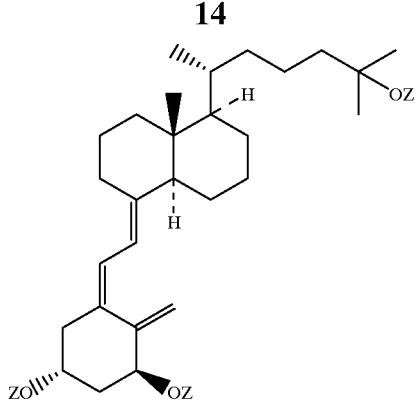

wherein Z is a protecting group.

6. A method of treating vitamin D dependent disorders comprising administering to a host in need of such treatment an effective amount of a compound of formula I

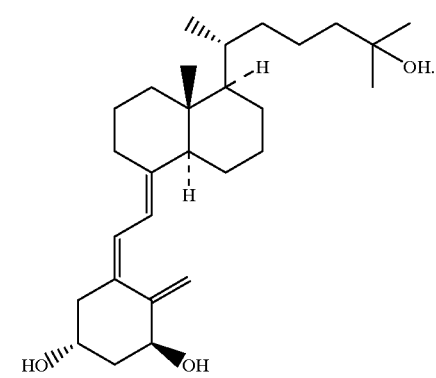

7. The method of Claim 6 wherein the vitamin D dependent disorder is psoriasis, leukemia, acne, seborrhoic dermatitis, osteoporosis or hyperparathyroidism.

* * * * *